US 8,283,646 B2

Oct. 9, 2012

(12) United States Patent
Murphy et al.

(54) FLAME DETECTOR PERSONALITY MODULE

(75) Inventors: James M. Murphy, St. Charles, IL (US); Scott R. Lang, Geneva, IL (US)

(73) Assignee: Honeywell International Inc., Morristown, NJ (US)

( * ) Notice: Subject to any disclaimer, the term of this patent is extended or adjusted under 35 U.S.C. 154(b) by 143 days.

(21) Appl. No.: 12/852,887

(22) Filed: Aug. 9, 2010

(65) Prior Publication Data

US 2012/0032097 A1    Feb. 9, 2012

(51) Int. Cl.
*F23N 5/08* (2006.01)
(52) U.S. Cl. .......................... 250/554; 356/437; 340/578
(58) Field of Classification Search .................. 250/554, 250/338.5; 356/437; 340/578
See application file for complete search history.

(56) References Cited

U.S. PATENT DOCUMENTS

| 5,081,998 | A | | 1/1992 | Yelderman et al. |
| 5,612,676 | A | * | 3/1997 | Plimpton et al. ............... 340/578 |
| 5,650,624 | A | | 7/1997 | Wong |
| 2002/0011570 | A1 | * | 1/2002 | Castleman ............... 250/339.15 |
| 2002/0122314 | A1 | | 9/2002 | Kojima et al. |
| 2008/0251724 | A1 | | 10/2008 | Baliga et al. |
| 2008/0296502 | A1 | * | 12/2008 | Kudoh .......................... 250/349 |

OTHER PUBLICATIONS

Partial European Search Report corresponding to Application No. EP 11 17 6863 dated Nov. 23, 2011.
European Search Report corresponding to Application No. EP 11 17 6863 dated Feb. 10, 2012.

* cited by examiner

*Primary Examiner* — Seung C Sohn
(74) *Attorney, Agent, or Firm* — Husch Blackwell LLP

(57) ABSTRACT

A flame detector includes a sensor module, which carries a plurality of pyroelectric sensors, and a filter module which carries a plurality of replaceable filters with one filter being associated with each sensor. The modules are coupled together and carried in an exterior housing. A cover can overlay the filters to retain them in predetermined positions relative to the respective sensors.

19 Claims, 6 Drawing Sheets

FLAME DETECTOR PERSONALITY MODULE

FIELD

The invention pertains to flame detectors. More particularly, the invention pertains to modular flame detectors which include interchangeable filter modules.

BACKGROUND

Known flame detectors of a type used in oil refineries and chemical plants often include triple band infrared sensing structures. Such flame detectors currently available in the marketplace are usually sold in fixed configurations. Customers order flame detectors that are either tuned to detect hydrocarbon fires (petroleum products) or non-hydrocarbon fires (hydrogen).

The detectors are tuned to either of these two fire types by the selection of particular wavelength filters that are placed in front of an infrared radiation sensor, such as, for example, a pyroelectric sensor. In known detectors, the filters are permanently affixed to the detectors. Infrared filters usually pass wavelengths of 2-6 microns. Known flame detectors often use three or four channels.

It would be advantageous to be able to easily change the sensing characteristics or, personality of the detector by quickly changing the set of filters in the product. The filters could be factory installable, or field installable.

DETAILED DESCRIPTION

Figure 1A:
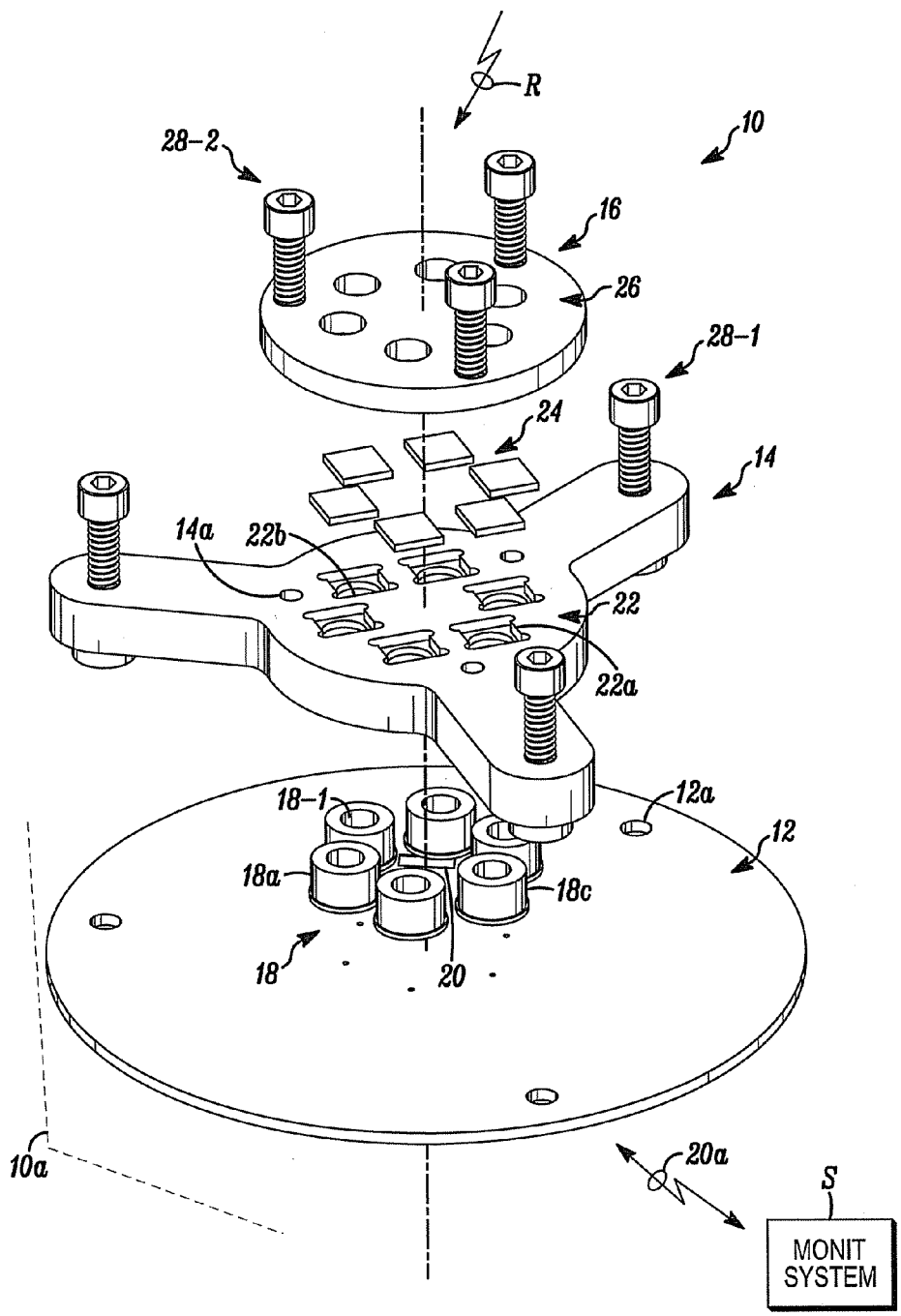
FIGS. 1A-1B are various views of a first embodiment of a detector which embodies the invention.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

In embodiments of the invention, a filter module holds a set of filters that establish the detector's personality, that is, which fires it is optimized to detect. The module can be fitted over broadband infrared or UV detectors that are mounted on a circuit board or any other component mounting member.

The set of filters, or, personality module, could either be changed by a customer or by a manufacturer (in order to be able to offer fewer SKU's). In another aspect of the invention, the filter module can be designed to hold up to six filters. It will be understood that the number of filters is not a limitation of the invention.

The filters can pass infrared or ultraviolet radiation, for example, based on the types of fires of interest. For example, a spectral range of 2-6 microns might be selected for multi-channel IR detectors having changeable filter modules.

In another aspect, and without limitation, two pieces of thin material, metal or plastic, can be used to sandwich the filters. The filters can be any size, but would, preferably be about 0.25 inches in diameter or along an edge. The material could be formed with a pocket or recess to hold the filter in the proper position relative to the respective infrared sensor. The filter-holder, or module, can then be keyed so that it can be plugged into the flame detector.

In a disclosed embodiment, the various modules can be coupled together by using fasteners, by providing threads and a screw-type attachment feature, or, by means of a snap-fit fastener structure. The modules can be installed in an external housing. Depending on the environment, an explosion proof housing can be used.

Control circuits could be mounted on a planar member, such as a printed circuit board along with the sensors. The filter module can overlay the printed circuit board and sensor module, and be attached thereto as discussed above. Such modular detectors could be coupled wirelessly or by cables to a monitoring system.

Figure 1B:
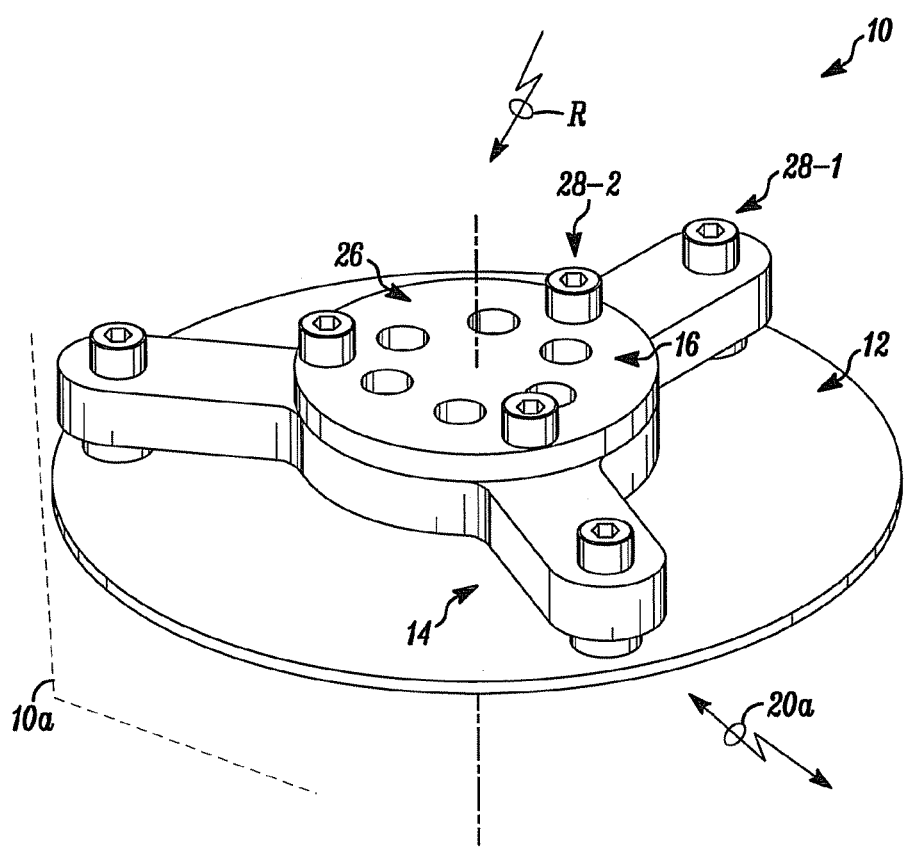

FIGS. 1A, 1B illustrate an embodiment of a flame detector 10 which embodies the invention. Detector 10 includes a mounting element 12, which could be a printed circuit board, a filter module 14 and a cover 16.

A plurality of pyroelectric sensors 18 is carried on the member 12. It will be understood that any appropriate type of radiant energy sensor could be used in the detector 10, without limitation. The type of sensor chosen is not a limitation of the invention.

Control Circuits 20 also carried on element 12 are coupled to members of the plurality 18, such as 18*a, b c* . . . . The control circuits 20 carry out processing of signals from the sensors 18 to determine the presence of fire. The control circuits 20 can also communicate wirelessly, or wired, as indicated at 20*a* with a displaced monitoring system S.

The filter module 14 includes a plurality of shaped openings, or recesses, 22 which can receive the various filters 24. The filters 24 are retained in position relative to optical inputs of sensors 18, such as 18-1, by a portion 22*a* of respective ones of the recesses 22. An optical path, such as 22*b* extends through each of the members of the plurality 22 to enable incoming radiant energy R, perhaps from a fire, which has passed through the various filters 24, to pass through the member 14 and be incident on the optical inputs 18-1 of the sensors 18.

As would be understood by those of skill in the art, the filters of plurality 24 would be selected to have optical characteristics consistent with the particular incident radiant energy R which is indicative of a type of fire, or fires of interest. Neither the composition, nor the shapes of the filters 24 are limitations of the invention. The members of the plurality 24 can be the same or different depending on the type of fire of interest as well as signal processing by circuits 20.

The cover 16 protects the filters 24 and retains them in position in the openings 22, in the recesses 22*a*. Openings 26 through the cover 16 provide a plurality of optical paths for incident radiant energy R to enter detector 10, pass through he filters 24, and the module 14 so as to be incident on the optical inputs of the sensors 18.

Elements 12, 14, 16 can be coupled together via fasteners, such as 28-1, 28-1, snap-fit members 28-2 as in embodiment 30, or snap-fit elements 38-2 of embodiment 50, all without limitation.

Alternately, threads can be formed on the members, such as 14, 16 which can be threadably coupled together without needing separate fasteners, such as 28-1, 28-2. It will be understood that the exact form of coupling of the elements 12, 14, 16 together is not a limitation of the invention.

The detector 10 can be carried in an explosion proof container 10*a*. As would be understood by those of skill in the art, connectors could be carried by the housing 10a to provide wired communication 20a to/from the monitoring system S.

Figure 2A:
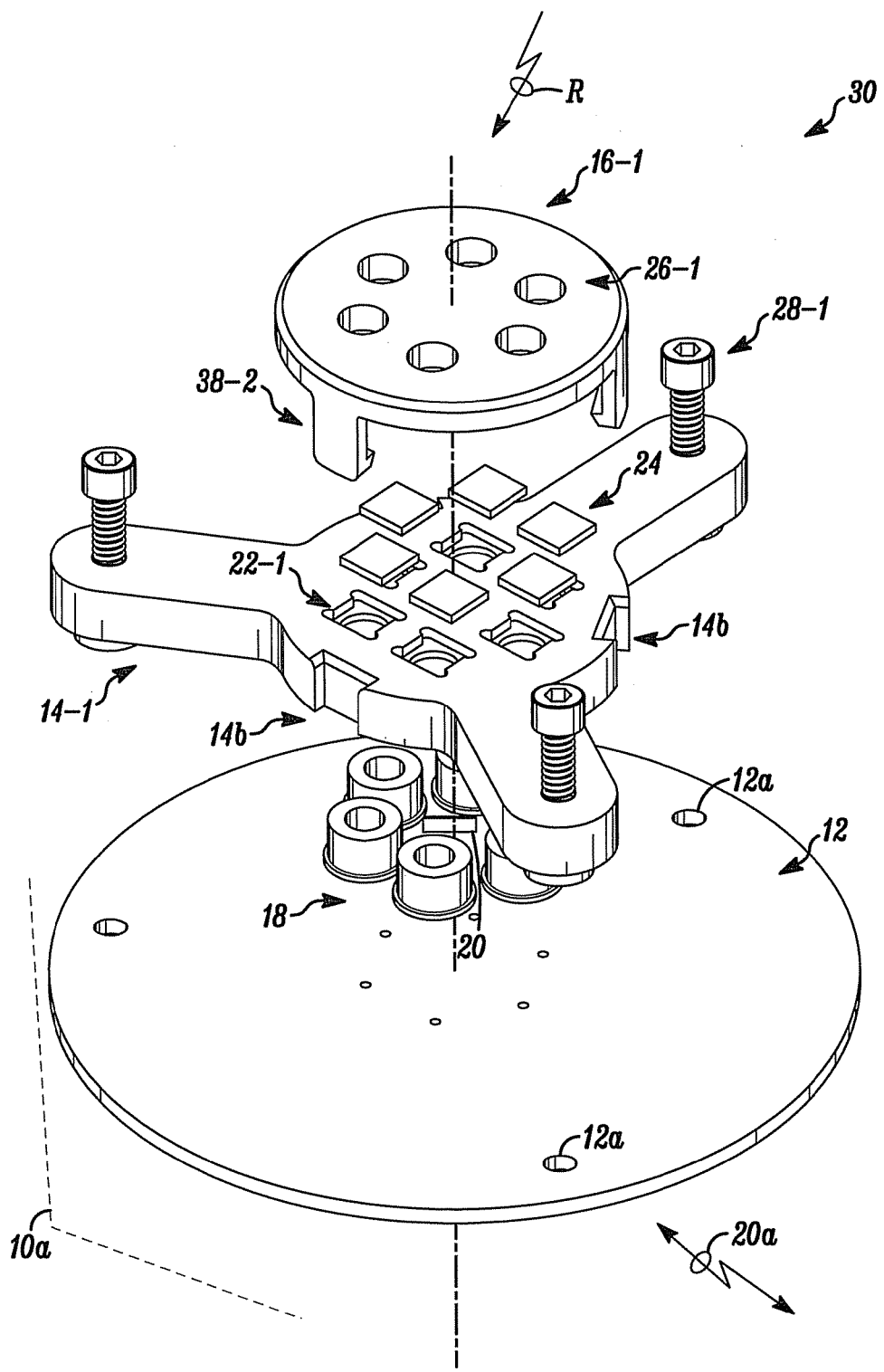
FIGS. 2A-2B are various views of a second embodiment of a detector which embodies the invention.
Figure 2B:
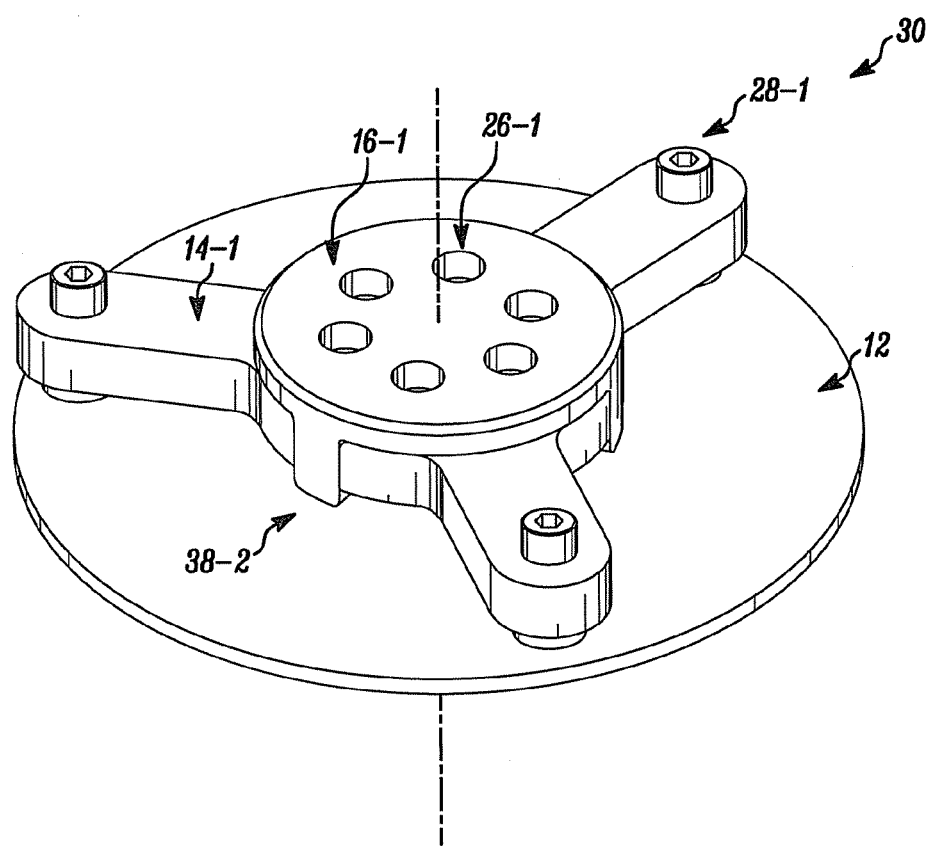
Figure 3A:
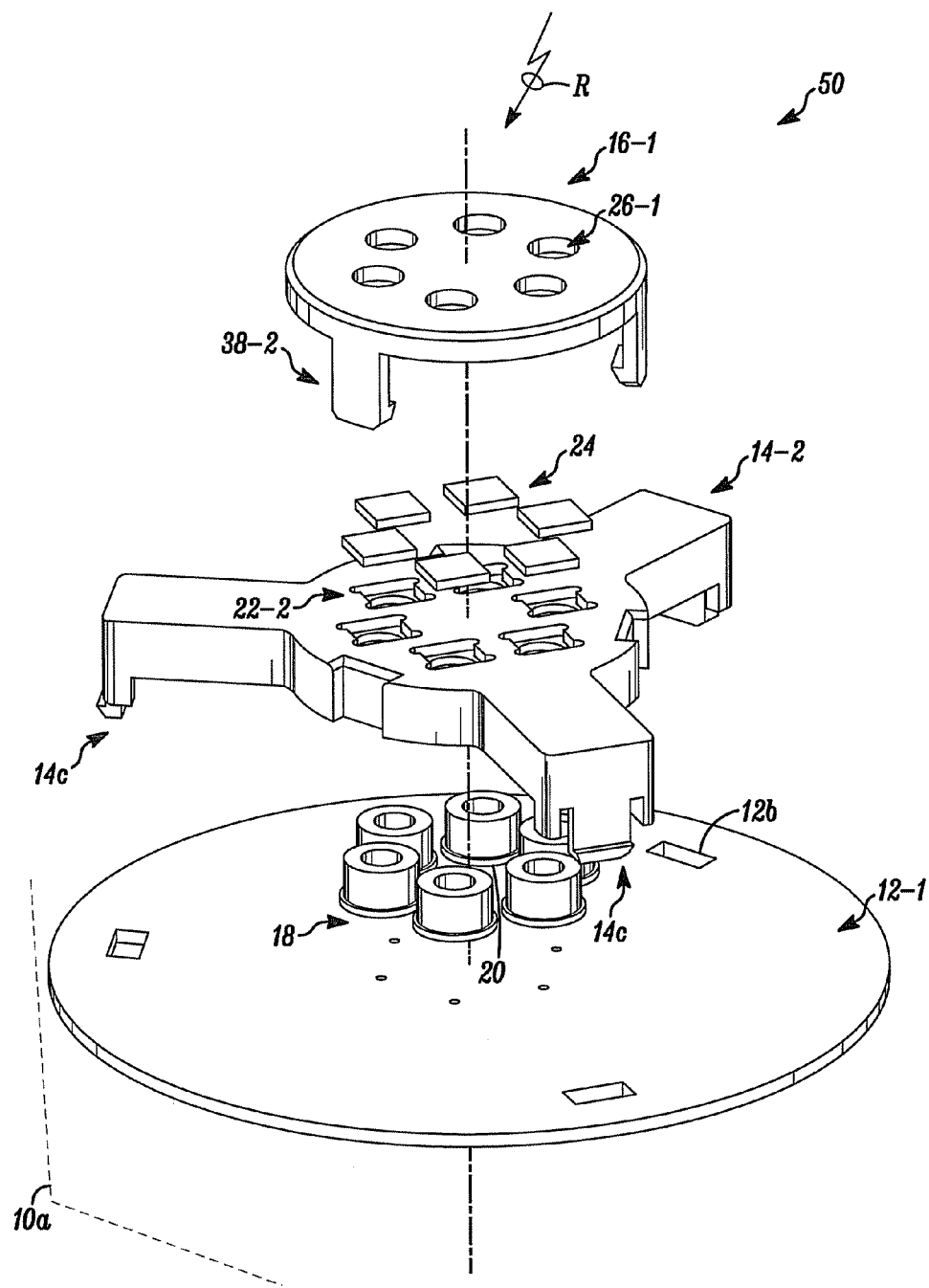
FIGS. 3A-3B are various views of another embodiment of a detector which embodies the invention.
Figure 3B:
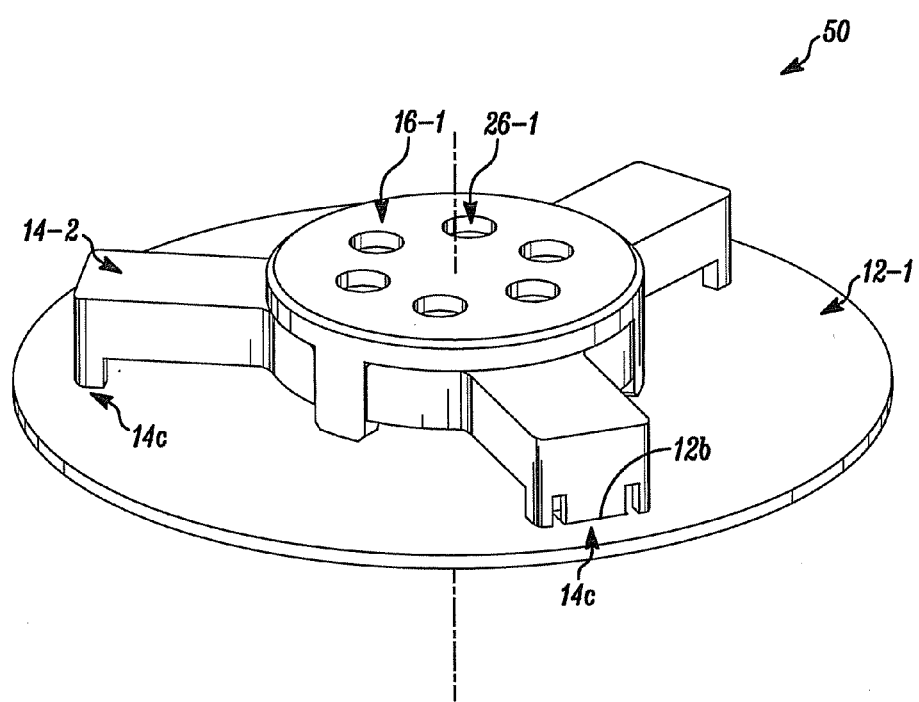

In the embodiment 30 of FIGS. 2A, 2B snap lock-type connectors 38-2 which engage slots 14b have been provided to lock the filter module 14-1 to the cover 16-1. In the embodiment 50 of FIGS. 3A, 3B filter module 14-2 is illustrated coupled to mounting member 12-1 by snap fit-type connectors 14c which engages slots 12b in the mounting plate 12-1. Other elements, as described above that appear in embodiments 30 and 50 have been assigned the same numerals in FIGS. 2A, 2B, 3A and 3B as in embodiment 10 of FIGS. 1A, 1B.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A modular flame detector comprising:
   a sensing module that carries a plurality of radiant energy sensors;
   a filter module that carries a plurality of different filters with each of the filters being associated with a respective one of the sensors, the filter module defining a first plurality of optical paths extending through respective ones of the filters; and
   a cover defining a second plurality of optical paths with each of the second plurality of optical paths being associated with a respective one of the first plurality of optical paths,
   wherein incident radiant energy enters the detector by passing through at least one of the second plurality of optical paths in the cover and reaches a respective one of the sensors by passing through a respective one of the first plurality of optical paths in the filter module.

2. A detector as in claim 1 which includes control circuits coupled to the sensors.

3. A detector as in claim 1 which includes an explosion proof hollow housing which carries the modules.

4. A detector as in claim 1 where the filters are removably carried by the filter module.

5. A detector as in claim 4 which includes control circuits coupled to the sensors.

6. A detector as in claim 2 where the control circuits process sensor outputs to make a flame determination.

7. A detector as in claim 2 where the control circuits evaluate output signals from the sensors indicative of different received spectral bands of radiant energy.

8. A detector as in claim 6 where the control circuits evaluate output signals from the sensors indicative of different received spectral bands of radiant energy.

9. A detector as in claim 6 which includes one of a wired or a wireless communications interface coupled to the control circuits.

10. A detector as in claim 2 where the sensors are carried on a planar mounting member along with the control circuits.

11. A detector as in claim 10 where the sensing module and the filter module are coupled together, at least in part, by one of fasteners, threads, or a snap fit-type connector.

12. A flame detector comprising:
    a housing;
    a sensor module which carries a plurality of radiant energy sensors;
    a filter module which carries a filter associated with each sensor, the filter module defining a first plurality of optical paths extending through respective ones of the filters;
    a cover defining a second plurality of optical paths, each of the second plurality of optical paths associated with a respective one of the first plurality of optical paths; and
    a coupling element for coupling the modules together,
    wherein incident radiant energy enters the detector by passing through at least one of the second plurality of optical paths in the cover and reaches an associated sensor by passing through a respective one of the first plurality of optical paths in the filter module.

13. A detector as in claim 12 where the sensing module and the filter module are coupled together, at least in part, by one of fasteners, threads, or a snap fit-type connector.

14. A detector as in claim 12 where the sensors comprise pyroelectric sensors.

15. A detector as in claim 12 where the filters have a spectral range of 2 to 6 microns.

16. A detector as in claim 12 where the filters are removably carried by the filter module.

17. A detector as in claim 16 which includes control circuits carried by the housing, where the circuits include a programmable processor and associated storage for executable instructions.

18. A detector as in claim 17 where the control circuits include an interface for communicating flame related information to a displaced monitoring system.

19. A detector as in claim 12 which includes at least one filter responsive to hydrocarbon-type fires and one filter that is responsive to hydrogen-type fires.

* * * * *